(12) United States Patent
O'Connor et al.

(10) Patent No.: US 7,400,259 B2
(45) Date of Patent: Jul. 15, 2008

(54) ACTIVITY MONITORING DEVICE

(75) Inventors: Gerard O'Connor, Chigwell (GB);
John Cahill, Country Cork (IE); Hugh Cahill, Perth (AU)

(73) Assignee: Product Systems Limited (GB)

( * ) Notice: Subject to any disclaimer, the term of this patent is extended or adjusted under 35 U.S.C. 154(b) by 255 days.

(21) Appl. No.: 11/405,742

(22) Filed: Apr. 18, 2006

(65) Prior Publication Data

US 2006/0255955 A1    Nov. 16, 2006

Related U.S. Application Data

(63) Continuation-in-part of application No. 10/474,892, filed as application No. PCT/GB01/05136 on Nov. 21, 2001, now abandoned.

(30) Foreign Application Priority Data

Aug. 8, 2001   (IE)   .................... S2001/0752

(51) Int. Cl.
*G08B 23/00*   (2006.01)

(52) U.S. Cl. ............ 340/573.1; 340/573.7; 340/539.12; 340/686.1

(58) Field of Classification Search ............. 340/573.1, 340/576, 573.7, 643.5, 539.12, 686.1, 691.1
See application file for complete search history.

(56) References Cited

U.S. PATENT DOCUMENTS

| 3,163,856 | A | 12/1964 | Kirby |
| 4,064,368 | A | 12/1977 | Dibner .......................... 179/5 |
| 4,536,755 | A | 8/1985 | Holzgang ................... 340/573 |
| 5,523,742 | A | 6/1996 | Simkins ...................... 340/573 |
| 5,754,121 | A | 5/1998 | Ward ..................... 340/870.09 |
| 5,941,836 | A | 8/1999 | Friedman .................... 600/595 |
| 6,445,298 | B1 | 9/2002 | Shepher .................. 340/573.1 |
| 6,646,556 | B1 | 11/2003 | Smith ....................... 340/573.1 |

*Primary Examiner*—George Bugg
*Assistant Examiner*—Travis R. Hunnings
(74) *Attorney, Agent, or Firm*—Renner, Kenner, Greive, Bobak, Taylor & Weber

(57) ABSTRACT

A device for monitoring the activity of a user to prevent deep vein thrombosis when travelling on transportation vehicles. The device comprises a carrier (20) for positioning on or adjacent a user, a motion sensor (10) mounted on the carrier (20) and adapted to detect the user performing a predefined motion, processor adapted to filter the motion detected to remove background motion not attributable to the desired exercise and to reset a timer (12) when the predefined motion is detected. An alarm (14) is operated by the processor should the time period elapse without the exercise pattern being detected. The components are all contained in the carrier (20) which is preferably a small container that can be attached to a user's trousers or around the limb of a wearer. Failure to undertake the required motion will cause the alarm (14) to be activated, thus notifying the wearer of the omission.

18 Claims, 6 Drawing Sheets

ACTIVITY MONITORING DEVICE

CROSS REFERENCE TO RELATED APPLICATIONS

This application is a continuation-in-part application of U.S. Ser. No. 10/474,892, filed Oct. 10, 2003 now abandoned, which is the national stage (under 35 U.S.C. 371) of International Application No. PCT/GB01/05136, filed Nov. 21, 2001.

BACKGROUND OF THE INVENTION

This invention relates to a device for monitoring the activity of a person travelling on a transportation vehicle and notifying that person of a specified pattern and frequency of their activity or inactivity, in order to reduce the risk of them developing deep vein thrombosis.

The present invention finds a particular use in the prevention of deep vein thrombosis (DVT), which is often caused by extended periods of inactivity, and it will be primarily described with reference thereto.

Deep vein thrombosis is a condition resulting from the lack of blood flow in the veins and the condition is related primarily, but not exclusively, to the legs. Blood flow tends to slow down or stop when there is prolonged inactivity, especially when seated, as would happen on a plane or any long journey in a cramped space. More specifically deep vein thrombosis occurs when a clot forms in the deep veins within the calf or thigh muscles. It is usually a spontaneous condition that occurs in people especially at risk, such as those with heart disease, those who smoke or consume alcohol and those that are generally overweight.

Any period of prolonged inactivity can generally trigger the condition and medical research suggests that those over forty years of age are at ever increasing risk. Warning signs are pain and tenderness in the leg muscles, redness and swelling of the skin. If the blood clot moves to the lung (a pulmonary embolus), then breathing difficulties can occur. A clot travelling on to the heart can cause death or if it travels to the brain a stroke is a possibility. There are well-documented cases of people suffering from this condition during long haul plane journeys and there have been some deaths attributed to DVT. In recent times a number of airline passengers have taken legal action against airline companies relating to this condition, and some companies are now putting warnings on their tickets.

The more cramped the condition, such as would occur in the economy class area of a plane, the more likely a person is to suffer from DVT, but recent medical research shows that the condition can occur to any class of traveller who does insufficient exercise.

It is to be expected that on a long haul flight lasting several hours that people will sleep for extended periods of this time. This cannot be prevented on an individual basis and this is where a problem may arise. Furthermore, due to the cramped conditions, people may at other times, for one reason or another remain essentially motionless. This inactivity reduces the blood flow in the legs and the potential problem of DVT becomes a factor.

Regular use of the legs during a journey dramatically reduces the risk of DVT. However, the transportation operators have no way of ensuring that suitable exercise is done by their passengers, despite the fact that the health and safety of those passengers is at least partially the airline operator's responsibility. The problem of DVT is not limited to airline travel, but is also encountered in other forms of transport such as cars, coaches and trains wherein prolonged periods of sedentary inactivity occur, usually in confined areas.

At present, the onus may be on travel operators to ensure that their passengers do not get DVT. However, the present type of traveller on long haul flights will clearly fit many of the conditions associated with DVT and as such can expose the travel operators to significant risk of negligence claims.

Previous attempts have been made to monitor the movement of patients such as those described in U.S. Pat. No. 5,941,836, U.S. Pat. No. 6,646,556, U.S. Pat. No. 4,536,755, U.S. Pat. No. 5,523,742, U.S. Pat. No. 4,064,368 and U.S. Pat. No. 6,445,298. None of these are designed for or suitable for use by passengers on transportation vehicles because they are large, cumbersome, suitable only for lying down and/or unable to distinguish relevant exercise movement from background movement caused by incorrect activity or the motion of the transportation vehicle.

BRIEF SUMMARY OF THE INVENTION

The present invention aims to provide a mechanism by which the motion or lack of motion of a person may be monitored and remedial action taken if the exercise is deemed inappropriate. In the context of DVT prevention it aims to reduce the risk of DVT occurring and move responsibility from the travel operators to the individual passenger by providing them with a device that will warn of lack of sufficient and suitable movement/exercise of the limbs.

The invention aims to provide a device that detects a deficiency in a traveller's exercise regime; alerts the traveller to the increased risk of DVT and promotes the appropriate exercise regime. To find utility in a transport setting the present invention provides a device that is small and portable enough to be used in a travel setting without compromising the comfort and safety of the travellers; that can detect a specific exercise in a vibration rich environment; can learn the appropriate exercise habits of an individual, calculate, and automatically adapt to reduce an individual traveller's risk; and is able to adjust its ability to detect exercise as the environment changes.

According to the present invention there is provided a transportation vehicle passenger activity monitoring device for monitoring the activity of a user travelling on a transportation vehicle, the device comprising a carrier adapted for releasable attachment to a user, a motion sensor mounted on the carrier to detect motion of the user; a processor also mounted on the carrier that receives motion information from the motion sensor and which differentiates motion attributable to the user performing a defined exercise from the overall pattern of motion detected, and an alarm adapted to be triggered should a time period elapse without the motion attributable to the user performing the defined exercise being detected, wherein the defined exercise and time period are such that the alarm is triggered if the user does not correctly exercised sufficiently frequently to reduce the risk of deep vein thrombosis, and wherein all of the components of the device are self contained on the user such that the device is portable within a transportation vehicle.

The processor may include a timer adapted to count the time period, and be reset if the user correctly performs the defined exercise. The timer may be a separate component linked to the processor.

The type of motion sensor used is important, and it is highly preferred that the motion sensor comprises a movable contact head mounted on a shaft, and contact plates at right angles to each other and adjacent the contact head to detect movement radially with respect to the shaft by contact of the head with the contact plates. The motion sensor may also include a calibration actuator that is in contact with the shaft and is able to detect vibrations and provide this data to the processor and which may also under control of the processor adjust the motion of the contact head. This can be used to minimize the effect of background vibrations. The calibration actuator may be linked to the processor to dynamically adjust the motion of the contact head to minimise the effect of background motion such as that caused by the transportation vehicle.

A small, discrete, self contained device is essential as it must be worn by a user without causing discomfort or danger. Therefore it is preferred that the carrier includes a shell within which the processor, motion sensor and alarm are mounted. This shell should also house all other components such as a power source.

The processor may preferably include a computer memory and software adapted to perform an analysis of data received from the motion sensor to differentiate the motion attributable to the user performing the defined exercise from the background motion. The software may be stored in the memory and run in the processor in several modes of operation. This may include: a learning mode in which specific performance of the defined exercise is detected and used to calibrate the device to minimise background motion; and a normal mode during which the calibrated device monitors the activity of the user on a journey.

The device may be further provided with a user interface to provide information to the user and/or to allow input by the user of information in to the device. Such user inputted information may include information selected from the group consisting of the user's height, the user's weight, the user's age and the user's lifestyle.

The device may be used to compliment other types of DVT prevention equipment. It is known to use an air bag exercise apparatus which can be used by a seated person to reduce risk of developing DVT. This apparatus relies on the user to undertake the exercise and so does not ensure that they are reminded to do so. The present invention also provides an exercise apparatus provided with an activity monitoring device as previously described which is adapted to monitor the correct use of the exercise apparatus and sound the alarm if insufficient or incorrect use is made of the apparatus. The apparatus could be a two chamber inflatable device, and this could also be provided with a pump for inflation thereof.

The device can monitor the activity of the entire body or of a specific limb and in order to monitor such activity it is essential that the sensor be positioned so that it may detect the movements of one or more part of the body. It is preferred that the sensor is held against the user and more particularly the limb of a user, and so the carrier may include an attachment means to permit removable attachment of the device to a user. Those attachment means may take any suitable form, but for attachment to a limb, they may comprise a strap that is adapted to pass around that limb. Such a strap may be made such that it may be stretched to pass over the hand or foot and then grip the limb once fastened. Alternatively the strap may be in two parts, the free end of each part being provided with means for inter-attachment, such as a two part hook and loop fastener (for example those sold under the trade name Velcro®), or a buckle. Releasable adhesive could also be used to fix the device to a limb or clothing. Ideally the device should be as small and easy to attach to the user as possible, it is therefore preferred that the carrier includes a mechanism for the releasable attachment to the user or the user's clothes. A catch or pin to engage the user's belt or clothes is highly suitable.

The motion sensor must be adapted to discern various patterns of movement characteristic of the defined exercise routine, from other motion that is either caused by the transportation vehicle or by the user. This allows the device to discern between different types of activity and only to record the performance of correct activity. This prevents the suppression of the alarm by insufficient or inappropriate movement.

Vibration can be classified into one or more of the following categories: periodic, random, resonant and harmonic. A periodic vibration repeats itself once every time period. In real terms dorsi and plantar flexion (which are suitable exercise motions) cause such once per cycle vibration which is periodic by nature. Random vibrations do not repeat themselves, and are not related to a fundamental frequency. An example in a plane might be hitting an air pocket, or in a car going over a pot hole.

Resonant vibrations occur at the natural frequency at which an airframe or mechanical system is inclined to vibrate. All things have one or more resonant frequency. Resonant vibrations are the result of a response in a mechanical system to a periodic driving force. Harmonic vibrations are exact multiples of a fundamental frequency.

The type of exercise motion that the motion sensor is adapted to monitor may be preset during manufacture, as may the time period for its completion. Such manufacture settings could adapt the device to a particular type of use (e.g. plane as compared to car) or user (e.g. overweight as compared to ideal weight). Alternatively, the type of predetermined motion and indeed the preset time period may be adjusted to allow the device to be swapped between different uses. This adjustment may be conducted by reprogramming the devices between different modes, using controls on the device or by control remotely from the device. The device may also be adapted to permit user interface, so that characteristics of the user, the transportation vehicle and the user's lifestyle can be input directly into the device to determine the required form, duration and frequency of exercise.

The alarm must be able to notify the user, and possibly persons other than the user, of the correct or incorrect activity, and may therefore, dependant on the end use, take several different forms. The alarm may include at least one of an audible signal generator such as a speaker, a light source such as a flashing LED, a vibrator such as is used in mobile phones and a transmitter connected to a remote notification system. Such a transmitter might be used when it is additionally, or alternatively, desired to notify a person other than the user (wearer) of the device.

Means for transmitting and/or receiving data may be included, either as part of the alarm, or in addition to the alarm, and these can allow remote control and monitoring of the device.

The device may be adapted for attachment to a person who desires to correctly carry out a specific exercise. In such an embodiment, the type of predetermined motion may be set to the pattern generated by the correct completion of the specific exercise routine, and the preset time period of the timer is set so that the alarm is triggered if the exercise is not correctly performed at the required frequency by the person wearing the device.

In a more sophisticated version of the invention the following sequence happens. A wearer will be given an alert on activation of the device. The alert might comprise the flashing of the LED, a buzz from a vibration motor or a message on a screen. The microprocessor could allow for the LED to flash in time with an exact exercise being achieved, in so doing it could train the wearer to do a specific regime of exercise. The LED will flash every fifteen seconds to show its wearer that it is functioning correctly.

In a further use of the LED, it could be that should the wearer refuse or fail to do the exercise in any one or more period of monitoring, then the flash rate of the LED could be changed by the processor to two flashes every fifteen seconds to indicate this. This has the function of alerting the crew of the transportation vehicle that the wearer refused or failed to do the determined exercise regime recommended.

The device would include a timer that can monitor activity over a suitable period such as fifty to sixty minutes and if insufficient/inappropriate exercise is detected in that period then it will cause a warning, such as three distinct buzzes of the vibration motor to warn a user to do the exercise regime.

On completion of the exercise another signal can be sent to the wearer, e.g. via the vibration motor, to indicate to the wearer that they can stop doing exercise. The device could then reset its clock and continue to monitor for a further fifty or sixty minutes.

According to the present invention there is also provided a method of preventing deep vein thrombosis in a passenger travelling on a journey in a transportation vehicle, the method comprising:

providing the passenger with a self contained activity monitoring device comprising a motion sensor to detect motion of the passenger; a processor that receives motion information from the motion sensor, and an alarm, the activity monitoring device being mounted on the passenger during the journey;

defining, on the basis of characteristics of the passenger, an exercise pattern to be performed, including a frequency time period for its repetition, to reduce the risk of deep vein thrombosis;

processing in the processor the motion detected by the motion sensor during the journey to differentiate motion attributable to the user performing the defined exercise pattern from the overall pattern of motion detected including the background motion caused by the transportation vehicle; and notifying the passenger, by means of the alarm, if insufficient or incorrect exercise is detected in order that the defined exercise pattern may be performed to reduce the risk of deep vein thrombosis.

The step of defining the exercise pattern may include the inputting in to the device by the passenger of information concerning their lifestyle and body characteristics (age, height, weight etc). This can be used to define a risk profile and so to determine an appropriate exercise pattern.

After the step of defining the exercise pattern, there may be a further step of placing the device in a calibration mode during which the passenger performs the defined exercise pattern (possibly but not essentially with minimal background motion). The particular vibration profile associated with the performance of the exercise by the passenger is detected and stored for use during the journey when the device is not in the calibration mode.

At least the step of processing the detected motion is preferably carried out by software stored in the device and running on the processor. This processing is at least a two stage process. The first stage filters the detected motion and dynamically calibrates the sensor to minimise background effects. This feeds motion information that is wholly or predominantly attributable to the activity of the user through to the second stage. The second stage analyses this motion for compliance with the defined exercise pattern in the time period. If this is detected the user is not notified, but if suitable activity is not detected the alarm may be triggered.

According to the present invention there is yet further provided a device for monitoring the activity of a user travelling on a transportation vehicle, the device comprising a carrier adapted for local attachment on or adjacent a user's leg by means of a releasable attachment device, a motion sensor mounted on the carrier and adapted to detect the user performing a predefined pattern of movement over a preset time frame, a timer mounted on the carrier and connected to the motion sensor so as to be reset should the motion sensor detect the predefined pattern of movement within the time frame, and an alarm also mounted on the carrier and connected to the timer for triggering thereby, should the timer count a preset time period without being reset, wherein the predefined pattern movement and the preset time frame of the timer are such that the alarm is triggered if the limb of the user is not correctly exercised sufficiently frequently to reduce the risk of deep vein thrombosis and wherein all of the components of the device are self contained on the user such that the device is portable within a transportation vehicle.

BRIEF DESCRIPTION OF THE DRAWINGS

In order that the present invention may be better understood, but by way of example only, various embodiments of the present invention will now be described in more detail with reference to the following drawings, in which.

DETAILED DESCRIPTION OF THE INVENTION

Figure 1:
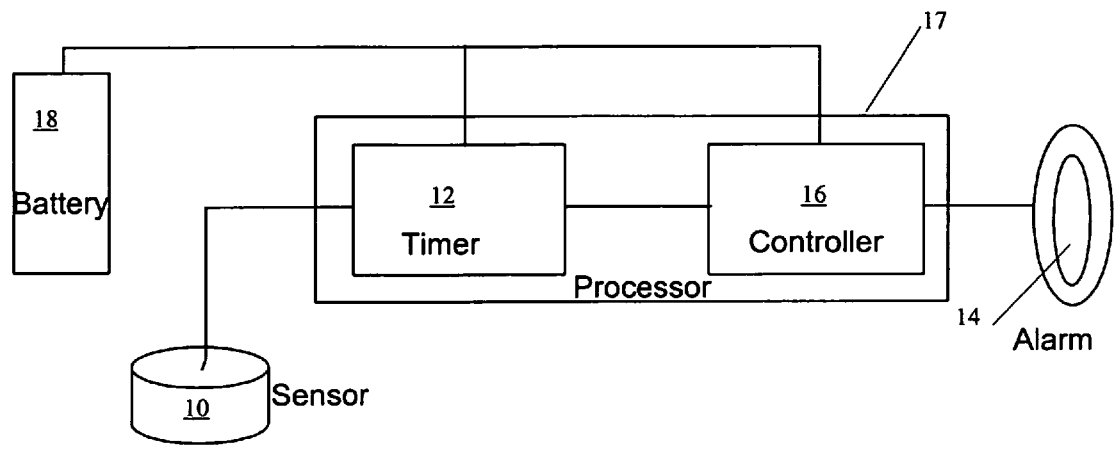
FIG. 1 is a simplified block schematic view of one embodiment of device according to the present invention.

FIG. 1 shows a simple schematic view a first embodiment of the present invention. The device comprises a motion sensor 10 positioned so that it may detect the movement of a user (not shown); a timer 12 connected to the sensor 10 and an alarm 14. The timer counts down a time period from a preset time t to zero (or up from zero to t), and when it reaches the end it cause operation of the alarm through a controller 16. The timer 12 and controller 16 are integrated within a processor 17. In the context of DVT prevention in airline passengers t may be 56 minutes. The motion sensor is adapted to detect a motion and the processor 17 discerns if the correct motion is detected and when it is detected, the timer 12 is reset to t. A power source in the form of a battery 18 powers the various components. The alarm may take several forms and indeed a device may include several different types in combination. For example a silent vibrating alert might be appropriate for a passenger on a plane to prevent annoyance to others.

Figure 2:
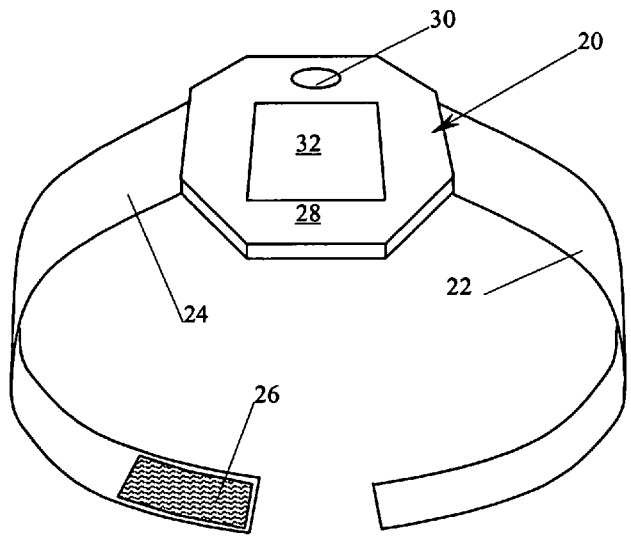
FIG. 2 is a perspective view of further similar embodiment in a form ready for use.

A more practical embodiment of device operating essentially as described with reference to FIG. 1 is shown in FIG. 2. In this embodiment the motion sensor, battery and processor are housed inside a carrier 20 which can be affixed to a wearer using the straps 22 and 24. The straps are passed around the leg (if using for DVT prevention) of a user and connected using a two part hook and loop fastener, one part of which 26 can be seen on the inner face of the strap 24. The carrier 20 is provided on its outer face 28 with an LED 30 which forms part of the alarm, and with an LCD screen 32 indicating operative information about the device such as the time until activation of the alarm or the number of alarm activations.

The device shown in FIG. 2 is intended for use by a passenger on a long journey, such as a long-haul airline flight. The device could be strapped to the ankle, leg or waist of a passenger using the straps 22 and 24 and the predetermined motion and time period will be set so as to detect regular motion suitable to reduce the chance of the passenger developing DVT. An example of appropriate exercise might be the tapping of the foot on the floor more than 180 taps in a 3 minute period to cause resetting of the timer. The length of the time period (t) that the timer counts down can vary, but for the prevention of DVT the exercise may comprise 180-240 foot taps in a three to four minutes period and repeated at least every 30 minutes to 1 hour (t=30 to 60 minutes). Dorsiflexion suggests the aforementioned range of taps is sufficient as in use on post op rehabilitation.

As long as the wearer performs the correct exercise regularly enough the timer will be reset and the alarm will not sound. Should correct movement NOT be detected then the timer will reach zero and trigger the alarm, thereby reminding the passenger to make the necessary exercise. The time period and type of exercise can be set by medical recommendation and by the characteristics of the user including height, weight, age and lifestyle.

The device could also detect other types of exercise that meet the criteria such as walking around and would also reset the counter in response to these. This minimises unnecessary activation of the alarm and prevents annoyance to the wearer. A range of devices could be provided on a plane with different preset values. Devices with different preset values could be colour-coded to allow the crew to make a distinction between different types of people. For example, people who could be at greater risk of DVT might be given a device with a shorter time period than those who are at less risk. It is envisaged that these devices with varying preset timing values could be distributed to the passengers at the commencement of the flight. During pre-flight safety demonstration their use could be described and demonstrated.

Simple embodiments of the device are automatic and require no adjustment or button pressing from either staff or passengers, as once they are preset the airline staff could literally hand them out in the same way, as for example, headphones are given out for onboard entertainment. In more advanced versions of the present invention the device can be adapted to define a suitable exercise pattern depending on the information provided by each user.

The LCD screen 32 could display the number of times the device has been reset by exercise. This information could be logged by the airline manually or automatically and then correlated to the seat position and passenger name. This would give the airline company a record of a particular passenger's compliance with the recommended exercise regime.

In practice, each passenger could be given this device and requested to wear it for their safety. Should they refuse or simply not use it then the airlines would have complied with the principle of providing as safe as possible a journey and the onus would shift on to the individual passenger.

Figure 3:
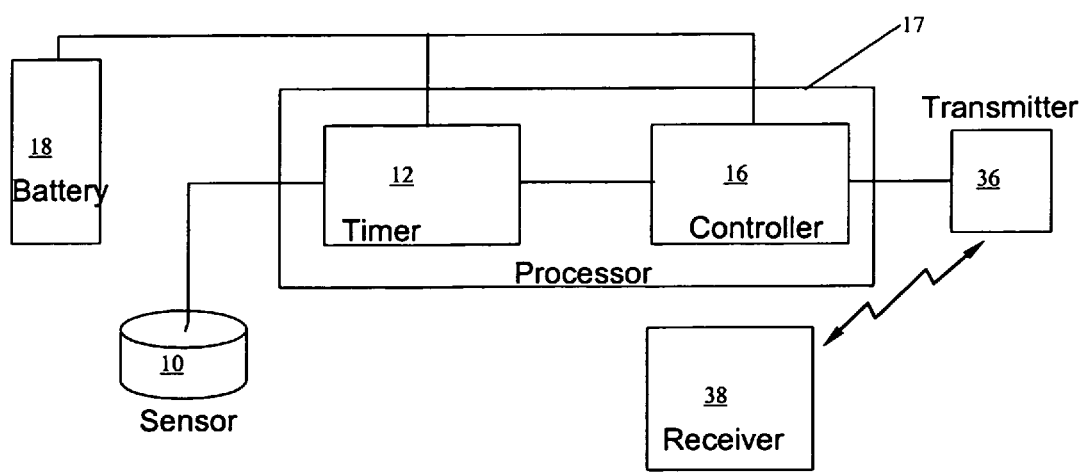
FIG. 3 is a simplified block schematic view of a further embodiment of device wherein the alarm comprises a low power transmitter, in communication with a remote monitoring station.

A small transmitter could be used in conjunction with the device and this is shown in FIG. 3. The embodiment of device in FIG. 3 is essentially similar to that shown in FIG. 1 and therefore like parts will be given like reference numerals. The difference between the two embodiments is that the alarm 36 in FIG. 3 includes a transmitter 36 in wireless communication with a receiver at a remote monitoring station 38. In this way the alarm signal may be transmitted to a remote location for monitoring by a third party. The transmitter could use low power radio waves or ultrasound to communicate with the remote monitoring station.

Figure 4:
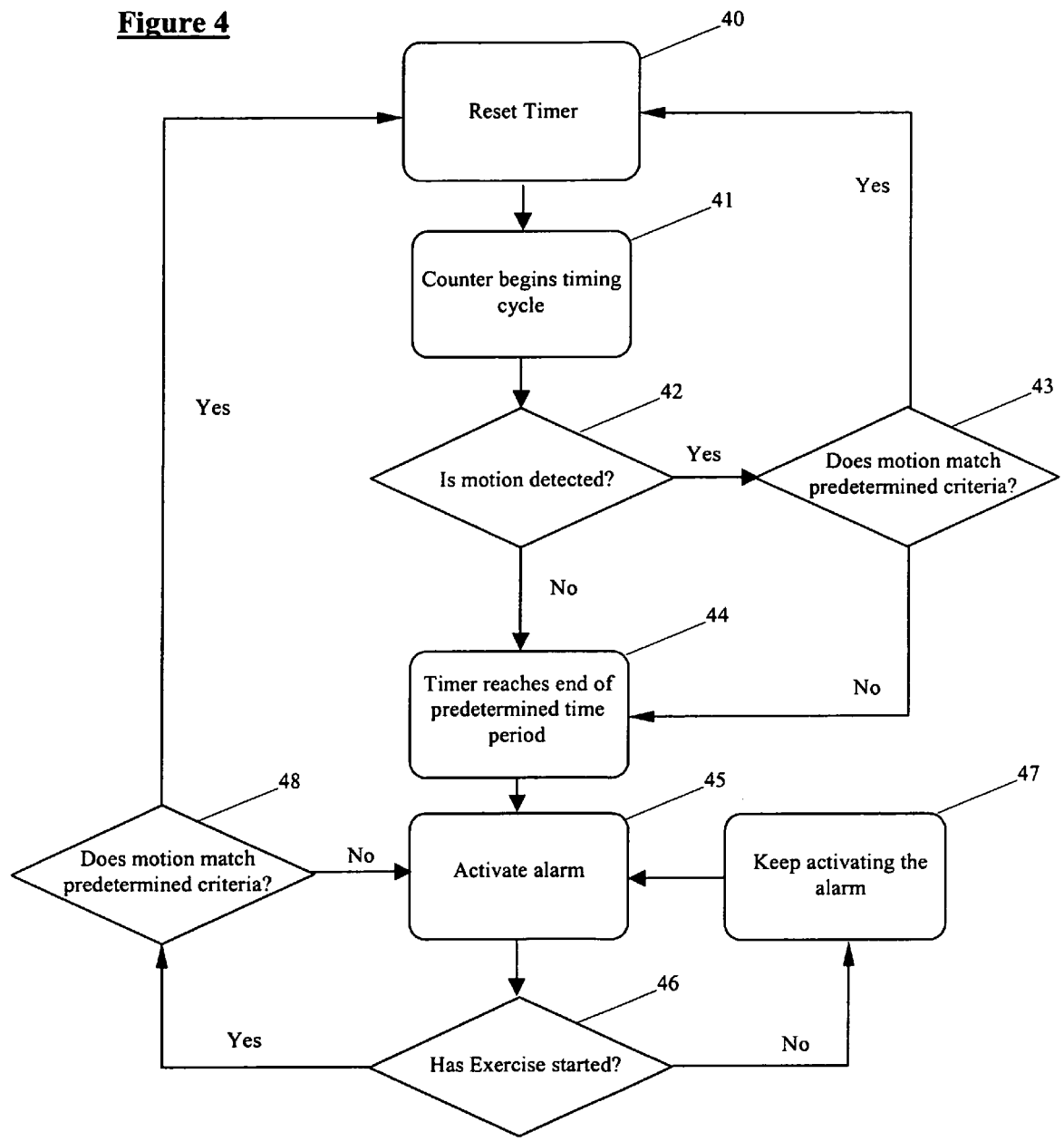
FIG. 4 is a flow chart to demonstrate operation of the embodiment of FIG. 1.

FIG. 4 is a flow diagram showing a simplified version of how an embodiment of device might operate. The device is initially attached to a wearer and reset at stage 40. The timer then begins counting down at step 41, whilst monitoring movement at step 42. If movement is detected the type of movement is analysed at step 43, and the movement associated with exercise is discerned from that attributable to background motion, and if it meets the criteria the timer is reset at stage 40. If the correct motion is not detected the timer reaches the end of the time period at step 44, and the alarm is activated at step 45. The motion sensor continues to monitor for activity at step 46, and whilst none of the correct pattern is detected, the alarm continues to activate at step 47. If exercise is detected, it is analysed at step 48, and if it meets the criteria the timer is reset at stage 40 to restart the cycle. If the exercise is not correct, the alarm will continue to be activated, unless it is manually cancelled.

Figure 5:
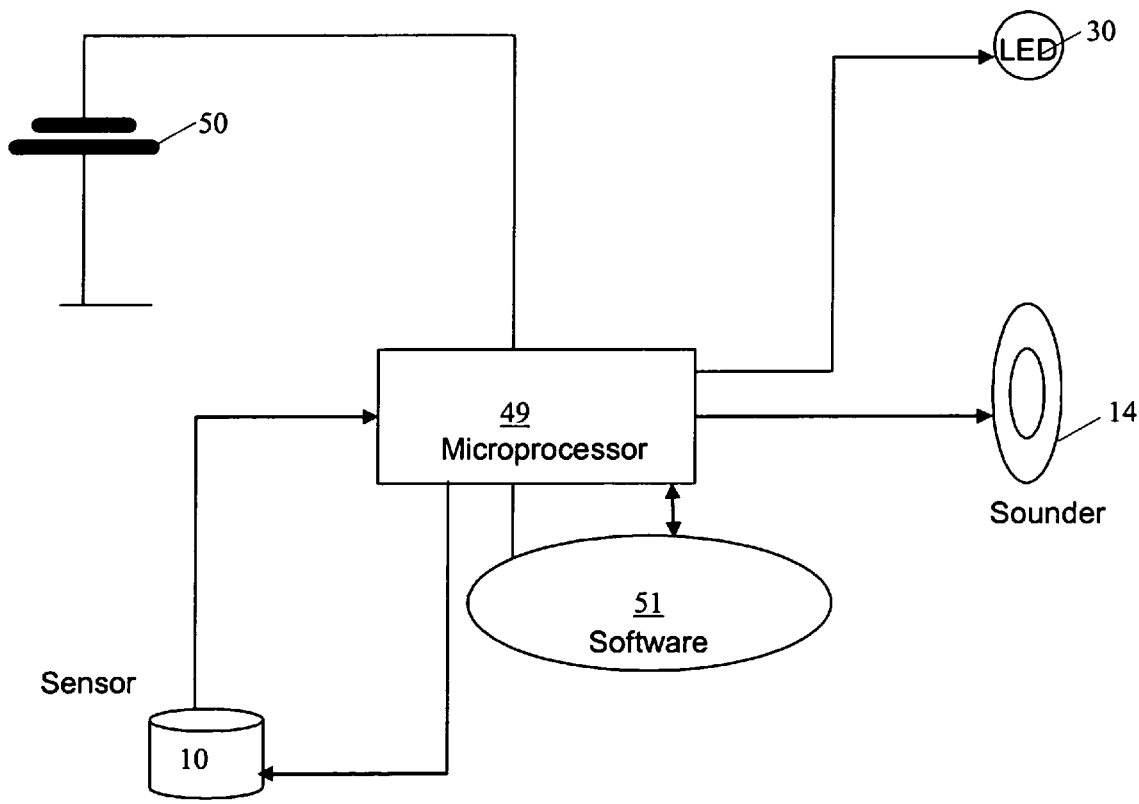
FIG. 5 is an alternative more sophisticated embodiment of the invention.

The embodiment in FIG. 5 comprises a microprocessor 49 on which driver electronics are run, and to which is fed motion data from the sensor 10. The sensor also receives feed back calibration information from the processor. An alarm comprising a sounder/vibration motor 14 and an LED 30 are driven by decisions made by software 51 running in the microprocessor 49. The LED 30 is used to alert the user that the device is functioning properly and also to alert that exercise over at least one period has not been carried out. This is achieved by changing of the LED flash pattern. A battery 50 provides power to the device.

Figure 6:
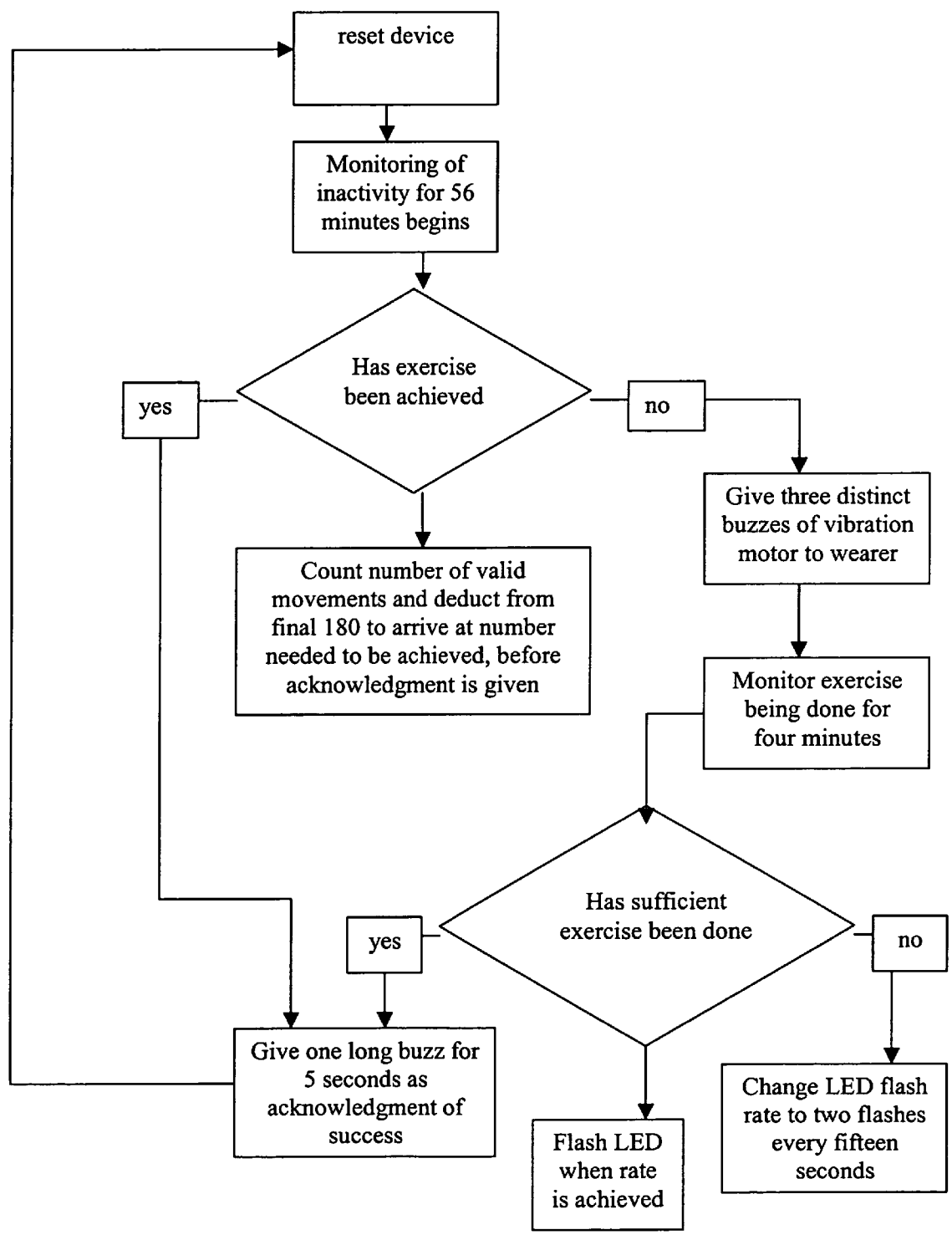
FIG. 6 is a flow chart to demonstrate the embodiment of the embodiment of FIG. 5.

The flow chart in FIG. 6 shows how the device in FIG. 5 might operate.

Figure 7:
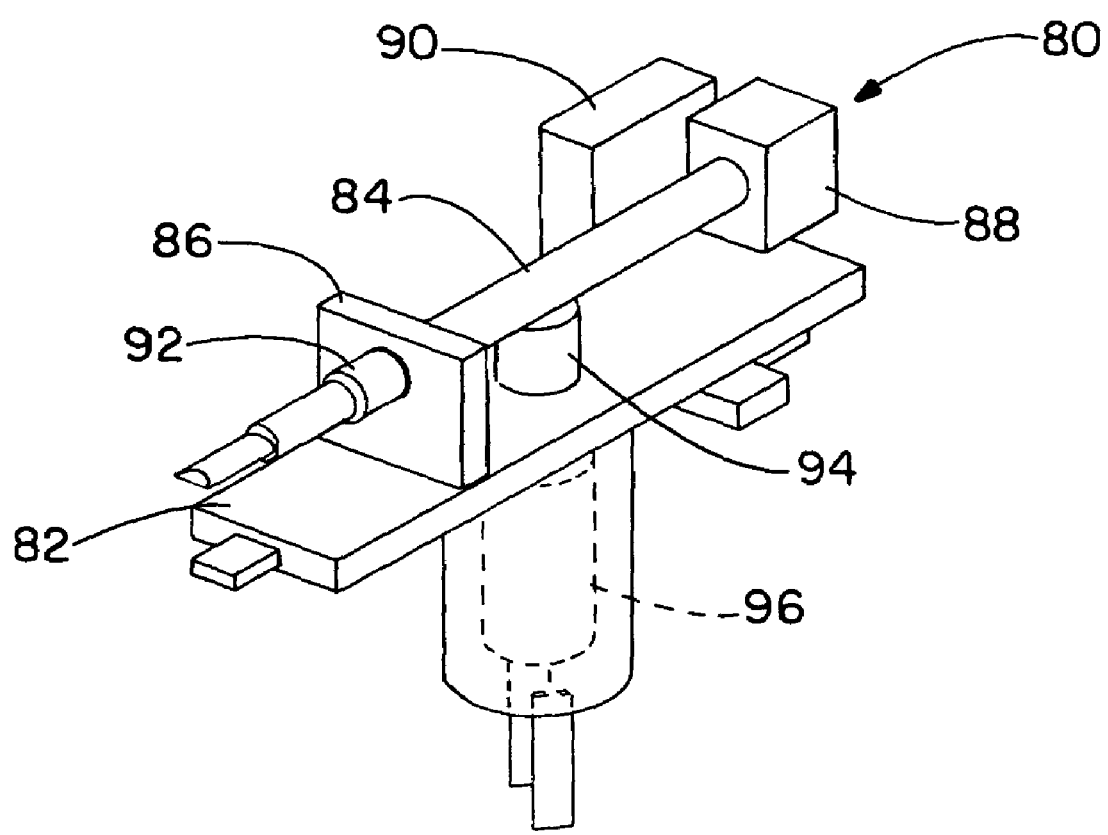
FIG. 7 is a simplified view of a motion suitable for use in the present invention.

An embodiment of motion sensor suitable for the present invention is shown in FIG. 7. The sensor comprises a hammer 80 mounted on a base 82 by location of a shaft 84 in an upstanding part 86. The hammer has a weighted metal contact 88, which when affected by vibration of significant amplitude completes an electrical circuit with at least one of a contact on the base 82 and a second contact 90 at ninety degrees to the base contact. The hammer is mounted by the shaft 84 which is insulated by an insulation sleeve 92 which covers the hammer shaft.

A solenoid controlled adjuster 94 is in contact with the hammer shaft 84. This can be used to adjust the sensitivity of the sensor and to transfer minute hammer movement to a solenoid coil in an adjuster actuator 96. This provides feedback on resonant and harmonic vibrations to the microprocessor, and the actuator 96 can be used to alter the motion of the hammer in response to the processor's control signals.

As mentioned above to use exercise to reduce the risk associated with DVT in a transport setting the present invention provides the following unique combination of qualities: 1) portable enough to be used in a travel setting without compromising the comfort and safety of the user or fellow passengers; 2) detects a specific exercise in a vibration rich environment; 3) can learn the appropriate exercise habits of an individual, calculate, and automatically adjust the exercise regime to reduce an individual traveller's risk; and 4) can adjust its ability to detect exercise as the environment changes.

To ensure the present invention is portable enough to use in a travel setting and not compromise the comfort and safety of the user and fellow passengers, the important design factors are: power consumption, processor size, passive component size, battery size, sensor size, motor size, and the manufacturing process.

The longest uninterrupted flight in regular schedule takes 18 hours, and the present invention has been tested to run for more than two weeks continuously using battery power. For present requirements, size no longer determines processor power or speed. Because of recent advances in chip design, microprocessors that meet our size, speed, and power requirements are readily available.

Battery size may preferably be approximately 23 mm diameter and 5.4 mm height. The sensor measures 20 mm in length×6 mm width×16 mm deep. The vibration actuator currently used is 16 mm length×6 mm in diameter. The manufacturing process uses chip on board combined with surface mount components.

Figure 8:
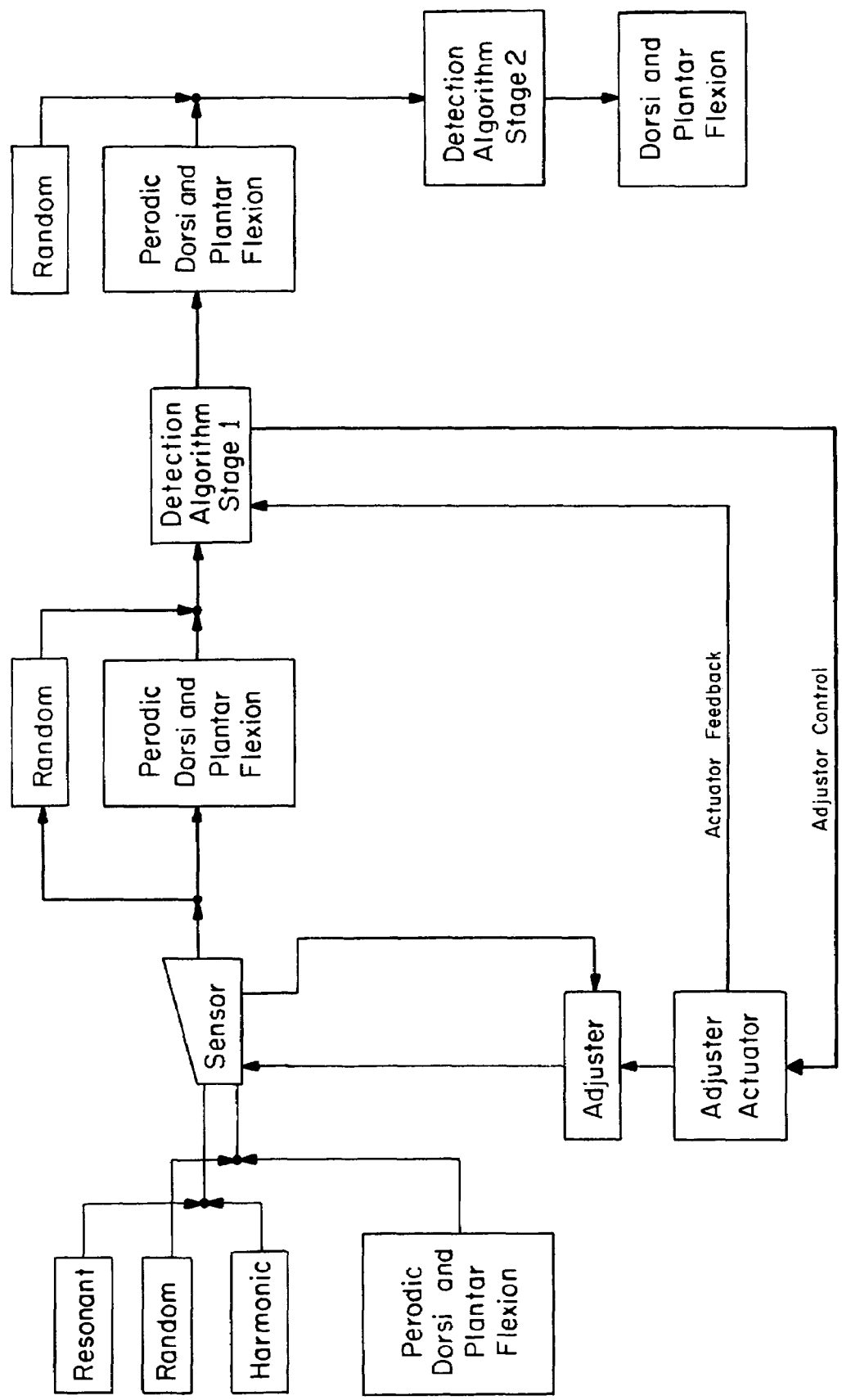
FIG. 8 is a flow chart to demonstrate the operation of a third embodiment of the present invention.

An exercise detection flowchart is shown in FIG. 8. In normal mode, vibrations of the various types feed through the sensor 10. The sensor's characteristics tend to filter out the resonant and harmonic vibrations, leaving the exercise (periodic vibrations) and some of the random portion of the vibration picture. This detected motion is feed into the microprocessor 17, and stage 1 of detection software running on the processor filters this to remove the random portion. The result of this clearly identifies whether the traveller is active or not and also how well, the sensor is coping with the resonant and harmonic portion of the vibration picture. The software in the processor uses the solenoid coil in the actuator 96 to detect and isolate changes in the vibration picture which are then referenced against the exercise being performed. After the processor finishes polling the actuator 96 it uses the same coil to drive the hammer adjuster 94 to adjust the sensitivity and calibration of the sensor as necessary. This unique twofold use of the actuator allows it dynamically to adjust the sensitivity of the sensor to cope with environmental changes in real time.

The software has a second stage process that monitors the frequency of the detected movement and compares it with the traveller's defined exercise profile. The second stage also uses this profile to help filter out any random vibration with amplitude great enough to pass through the stage 1 filter.

The device has a training mode which allows it to learn the relevant exercise habits of an individual passenger and automatically to adjust the exercise regime to reduce their DVT risk. During the initial training mode the passenger is asked to perform a series of movements. This data is then used to form part of the traveller's profile. In an advanced embodiment the traveller can interact with the device through a user interface such as an LCD screen and buttons. This interaction allows the traveller to enter information that helps determine their DVT risk. The software combines this with the other data to develop a profile for the traveller, and thereby to adjust the defined exercise regime appropriately.

The background motion caused on a transportation vehicle can alter on different journeys or indeed during the same journey. The present invention can automatically adjust its ability to detect exercise as the environment changes. This is achieved this by using two-way interactive feedback between the processor and the sensor (see FIG. 8). As conditions change, feedback from the actuator allows the sensor to be automatically adjusted which reduces the effects of background motion on the sensor.

The invention claimed is:

1. A transportation vehicle passenger activity monitoring device for monitoring the activity of a user travelling on a transportation vehicle, the device comprising a carrier adapted for releasable attachment to a user, a motion sensor mounted on the carrier to detect motion of the user; a processor also mounted on the carrier that receives motion information from the motion sensor and which differentiates motion attributable to the user performing a defined exercise from the overall pattern of motion detected, and an alarm adapted to be triggered should a time period elapse without the motion attributable to the user performing the defined exercise being detected, wherein the defined exercise and time period are such that the alarm is triggered if the user has not correctly exercised sufficiently frequently to reduce the risk of deep vein thrombosis, and wherein all of the components of the device are self contained on the user such that the device is portable within a transportation vehicle.

2. A device as claimed in claim 1 wherein the processor includes a timer adapted to count the time period, and be reset if the user correctly performs the defined exercise.

3. A device as claimed in claim 1 wherein the motion sensor comprises a movable contact head mounted on a shaft, and contact plates at right angles to each other and adjacent the contact head to detect movement by contact of the head with the contact plates.

4. A device as claimed in claim 3 wherein the motion sensor includes a calibration actuator that is in contact with the shaft and is able to detect vibrations and adjust the motion of the contact head.

5. A device as claimed in claim 4 wherein the calibration actuator is linked to the processor and dynamically adjusts the motion of the contact head to minimise the effect of background motion such as that caused by the transportation vehicle.

6. A device as claimed in claim 1 wherein the carrier includes a shell within which the processor, motion sensor and alarm are mounted.

7. A device as claimed in claim 1, in which carrier is adapted for attachment to a user's clothes.

8. A device as claimed in claim 1, in which the defined exercise processor is adapted to detect and/or the time period may be adjusted.

9. A device as claimed in claim 1, in which the alarm includes at least one of an audible signal generator, a light source, and a vibrator.

10. A device as claimed in claim 1, in which the processor includes a computer memory and software adapted to perform an analysis of data received from the motion sensor to differentiate the motion attributable to the user performing the defined exercise from the background motion.

11. A device as claimed in claim 10, in which the software running in the processor defines several modes of operation including: a learning mode in which specific performance of the defined exercise is detected and used to calibrate the device to minimise background motion; and a normal mode during which the calibrated device monitors the activity of the user on a journey.

12. A device as claimed in claim 1, in which there is further provided a user interface to provide information to the user and/or to allow input by the user of information.

13. A device as claimed in claim 12, wherein the user interface allows input of information selected from the group consisting of the type of transportation vehicle, the user's height, the user's weight, the user's age and the user's lifestyle.

14. A device as claimed in claim 1, which also includes means for transmitting data concerning the activity of the user.

15. A device as claimed in claim 1, which also includes means for receiving data, such as data concerning the user.

16. A method of preventing deep vein thrombosis in a passenger travelling on a journey in a transportation vehicle, the method comprising:
   providing the passenger with a self contained activity monitoring device comprising a motion sensor to detect motion of the passenger; a processor that receives motion information from the motion sensor, and an alarm, the activity monitoring device being mounted on the passenger during the journey;
   defining, on the basis of characteristics of the passenger, an exercise pattern to be performed, including a frequency time period for its repetition, to reduce the risk of deep vein thrombosis;
   processing in the processor the motion detected by the motion sensor during the journey to differentiate motion attributable to the user performing the defined exercise pattern from the overall pattern of motion detected including the background motion caused by the transportation vehicle; and
   notifying the passenger, by means of the alarm, if insufficient or incorrect exercise is detected in order that the defined exercise pattern may be performed to reduce the risk of deep vein thrombosis.

17. A method as claimed in claim 16, wherein the step of defining the exercise pattern includes the inputting in to the device by the passenger of information concerning their lifestyle and body characteristics.

18. A method as claimed in claim 16, wherein after the step of defining the exercise pattern, there is a further steps of placing the device in a calibration mode whilst the passenger performs the desired exercise pattern, detecting a particular vibration profile associated with the performance of the exercise by the passenger and storing that detected pattern for use during the journey when the device is not in the calibration mode.

* * * * *